(12) United States Patent
Lechner

(10) Patent No.: US 8,622,888 B2
(45) Date of Patent: Jan. 7, 2014

(54) SYSTEM FOR CONTROLLING A CONTROLLABLE STOMACH BAND

(76) Inventor: Wolfgang Lechner, Pixendorf (AT)

( * ) Notice: Subject to any disclaimer, the term of this patent is extended or adjusted under 35 U.S.C. 154(b) by 914 days.

(21) Appl. No.: 12/085,538

(22) PCT Filed: Dec. 21, 2006

(86) PCT No.: PCT/AT2006/000529
§ 371 (c)(1),
(2), (4) Date: May 27, 2008

(87) PCT Pub. No.: WO2007/070906
PCT Pub. Date: Jun. 28, 2007

(65) Prior Publication Data
US 2009/0306462 A1    Dec. 10, 2009

(30) Foreign Application Priority Data

Dec. 22, 2005    (AT) .................. A 2058/2005

(51) Int. Cl.
*A61F 2/02*    (2006.01)
(52) U.S. Cl.
USPC ............................................. 600/37
(58) Field of Classification Search
USPC ............. 600/37; 604/891.1, 892.1; 606/151, 606/157, 191, 192; 607/40, 60
See application file for complete search history.

(56) References Cited

U.S. PATENT DOCUMENTS

| | | | |
|---|---|---|---|
| 4,592,339 A | | 6/1986 | Kuzmak et al. |
| 5,081,987 A | * | 1/1992 | Nigam ............................ 607/19 |
| 5,701,894 A | * | 12/1997 | Cherry et al. ................. 600/300 |
| 6,067,473 A | * | 5/2000 | Greeninger et al. ............ 607/32 |
| 6,475,136 B1 | | 11/2002 | Forsell |
| 6,966,875 B1 | | 11/2005 | Longobardi |
| 2002/0123672 A1 | * | 9/2002 | Christophersom et al. ... 600/300 |
| 2002/0161414 A1 | * | 10/2002 | Flesler et al. ................... 607/40 |
| 2003/0135120 A1 | * | 7/2003 | Parks et al. .................... 600/463 |
| 2004/0064110 A1 | * | 4/2004 | Forsell ..................... 604/288.01 |

(Continued)

FOREIGN PATENT DOCUMENTS

EP    1 736 123    12/2006
WO    01/12078    2/2001

(Continued)

OTHER PUBLICATIONS

Lechner, Wolfgang, et al. "In Vivo Band Manometry: a New Access to Band Adjustment." *Obesity Surgery* (2005) pp. 1432-1436.

*Primary Examiner* — Christine Matthews
*Assistant Examiner* — Joshua D Lannu
(74) *Attorney, Agent, or Firm* — Ladas & Parry LLP

(57) ABSTRACT

A system for controlling a controllable gastric band (1), having a control unit (11), wherein the gastric band (1) includes a nonextensible back (4) and a chamber (2) arranged on the stoma side of the back and capable of being filled with a fluid, which chamber is in connection with a second chamber (5) and has at least one sensor (7) for the detection of the pressure on the gastric wall. The sensor (7) can be connected with a device (8) for the wireless transmission of the detected pressure values to the control unit (11). The control unit (11) can include a device (13) for receiving transmitted pressure data from the at least one sensor (7). Also, at least one memory (9, 14) for storing the pressure values detected and a device (16) for processing the time courses of the pressure values detected.

28 Claims, 3 Drawing Sheets

(56) References Cited

U.S. PATENT DOCUMENTS

| | | |
|---|---|---|
| 2004/0152957 A1* | 8/2004 | Stivoric et al. ............... 600/300 |
| 2004/0176822 A1* | 9/2004 | Thompson et al. ............ 607/60 |
| 2005/0065450 A1* | 3/2005 | Stuebe et al. ................. 600/547 |
| 2005/0143765 A1* | 6/2005 | Bachmann et al. .......... 606/157 |
| 2006/0183967 A1 | 8/2006 | Lechner |
| 2006/0199997 A1* | 9/2006 | Hassler et al. ................. 600/37 |
| 2009/0118572 A1 | 5/2009 | Lechner |

FOREIGN PATENT DOCUMENTS

| | | |
|---|---|---|
| WO | 01/12078 A1 | 2/2001 |
| WO | WO 0112078 A1 * | 2/2001 |
| WO | 2004/014245 | 2/2004 |
| WO | WO 2004014245 A1 * | 2/2004 |
| WO | 2005/009305 | 2/2005 |
| WO | 2005/009305 A1 | 2/2005 |
| WO | 2006/113187 | 10/2006 |
| WO | 2006/118793 | 11/2006 |
| WO | 2006/122285 | 11/2006 |

* cited by examiner

SYSTEM FOR CONTROLLING A CONTROLLABLE STOMACH BAND

The invention relates to a system for controlling a controllable gastric band, comprising a control unit, wherein the gastric band includes a nonextensible back and a chamber arranged on the stoma side of the back and capable of being filled with a fluid, which chamber is in connection with a second chamber and has at least one sensor for the detection of the pressure on the gastric wall, and wherein the sensor is connected with a device for the wireless transmission of the detected pressure values to the control unit, and wherein the control unit includes a device for receiving transmitted pressure data from the at least one sensor of the gastric band, as well as a housing.

Controllable gastric bands in which the supply of liquid into the chamber, and the discharging of liquid from the chamber, is achieved by puncturing a subcutaneously fixed chamber, a so-called port, which is connected with the chamber of the gastric band via a suitable duct, are offered by numerous manufacturers in basically identical configurations. Such a gastric band is a medical implant used to restrict food intake and hence reduce weight, which is wrapped around the uppermost stomach portion and closed.

U.S. Pat. No. 6,966,875 B1 describes a gastric band which is placed around the stomach like a belt and secured. An adjustment of the restriction of the stoma is feasible merely mechanically by contracting the band.

U.S. Pat. No. 4,592,339 A describes a gastric band in which a chamber is arranged on the band side facing the stomach, which chamber can be filled with a liquid. A control of the stoma width is thereby enabled. The filling with liquid and emptying of the system may be realized via a subcutaneously sewn-in port, which is connected with the chamber of the gastric band via a hose.

WO 2004/014245 A1 describes a controllable gastric band, in which the displacement of liquid from a port into the chamber of the gastric band may be effected from the outside by means of a remote control.

Recent researches have shown that the internal pressure of the band very precisely reflects the peristaltic of the esophagus. These pressure data enable a very precise adjustment of the optimum stoma width. Pressure curves also provide information on how long and how often a person eats and drinks. Therefore, the internal pressure of the band is very well suited for various control purposes in connection with the application of gastric bands (W. Lechner et al.: In Vivo Band Manometry: a New Access to Band Adjustment. Obesity Surgery, 15, 1432-1436, 2005).

The stomach bands presently in use in most cases yield very good long-term results in terms of weight reduction and patient satisfaction. Yet, there are some problems, which become particularly prominent with high band fillings. Many patients have, thus, reported on unpleasant phenomena like sialemesis and regurgitation, particularly in the recumbent position. Food particles may remain in the esophagus above the stoma for quite some time, start fermenting there and hence provoke, in addition to bad breath, an irritation of the mucous membrane involving pain. A permanently too strong contraction of the band will over months lead to a motoric exhaustion of the esophagus, which will finally end up in a massive expansion of the esophagus. The swallowed food will no longer be conveyed into the stomach through the stoma by peristaltic contraction waves, but by the gravity of the swallowed food piling up above the band. Such a condition must be prevented by all means, since it will be accompanied by a loss of the sense of fullness. Consequently, the effect of the band will be lost, which will then lead to an increase in weight despite the highly filled gastric band provided. On account of the long residence time of food particles in the esophagus, various problems such as retrosternal burning or "heartburn" and the relapsing aspiration of food particles will additionally arise.

WO 2005/009305 A1 relates to a controllable stomach band, in which the above-mentioned problems are to be overcome by an autoregulatory change of the stoma width. They are based on changes of the internal pressure of the band in connection with the peristaltic of the esophagus during the eating process. The bolus is pressed through the gastric band by peristaltic waves. This causes a pressure increase in the chamber of the gastric band, which can be used to control the pressure of the gastric band.

WO 01/12078 A1 shows a control system of the present kind, wherein the pressure values on the gastric wall are detected and transmitted to a control unit. When the predefined pressure values are exceeded or fallen short of, the filling of the gastric band is correspondingly changed. Yet, the current pressure values on the gastric wall are not suited for an immediate adjustment of the band width of the gastric band.

U.S. Pat. No. 6,475,136 B1 describes a controllable gastric band, in which an implantable pressure sensor detects the pressure on the gastric wall and uses the same for controlling the band adjustment.

The pressure in the gastric band during an eating process has already been acquired under clinical conditions. In order to obtain sufficient information, measurements are, however, to be carried out over at least half an hour and at repeated time intervals, which is time-consuming and stressing for the patient. Besides, waiting periods will, as a rule, apply after the recording of the data, before the data will be evaluated by the attending physician and the steps to be taken will be defined.

Alternatively, or additionally, X-ray examinations are performed after the administration of a contrast medium, which are substantially quicker than in-vivo measurements of the band internal pressure. These measurements, however, constitute a strain on the patient because of X-ray exposure and, moreover, involve high costs.

The object of present invention, therefore, consists in providing an above-mentioned system for controlling a controllable gastric band, which enable the simple monitoring of the pressure in the gastric band with little strain on the patient. The present invention is to eliminate or reduce the problems so far occurring with gastric bands having no autoregulatory functions.

This object according to the invention is achieved in that a memory for storing the pressure values detected and a device for processing the time courses of the pressure values received are provided. Such a system enables the pressure on the gastric wall to be detected continuously or during particular events, preferably during eating and to be transmitted to a control unit in a wireless manner. The transmission of the detected pressure values may occur permanently, or a given number of data can be temporarily stored and wirelessly transmitted to a control unit upon request. The patient need not receive outpatient treatment in order to acquire the pressure values, but the relevant data are collected during daily routine or even during night. By the preferably continuous monitoring of the pressure in the gastric band, the problems faced with presently used gastric bands having no autoregulatory functions will be overcome. The pressure by which the gastric band, or the fluid-filled chamber, is pressed at the stomach, plays a key role in what is called gastric banding. The band internal pressures reflect the extent of flow blockage and, in particular, the effect of flow blockage on the motor function of the esophagus. In the at least one memory the values may be temporarily stored and, upon request, transmitted for evaluation purposes. Such a memory may also serve for temporarily storing the pressure values in the event of an operating failure so as to prevent the loss of relevant data. The results provide the patient or the attending physician or the like with relevant information. By the inventive system, a control of physiological parameters, which are important as regards gastric banding, is achieved. The control system enables the motoric function of the esophagus to be monitored in a simple manner and with little stress on the patient.

Swallowing acts cause pressure increases in the gastric band. The peristaltic wave conveys a bite through the band into the stomach. The mentioned pressure increase in the band system occurs during a stoma passage. The amplitude of the pressure increase in the gastric band depends on the amplitude of the peristaltic wave, the extent of flow blockage and the viscosity of the bite. If a bite does not completely pass the band and part of it is, therefore, left in the esophagus, secondary peristaltic waves will form, i.e., peristaltic waves caused by the expansion of the esophagus due to the bite having been left, rather than by a swallowing act. Secondary peristaltic waves will prevail until the esophagus has been purged from the bite. These procedures can be pursued by way of the band internal pressure. By a preferably continuous detection of the pressure course in the band interior, the motoric function of the esophagus can be precisely monitored. Too narrow a band adjustment will cause food particles to remain above the band over a very long period of time, thus constantly triggering a secondary peristaltic activity, which will finally lead to the motoric exhaustion of the esophagus. This is exactly what can be prevented by pressure monitoring. When contracting the band, the physician may go to the limits of tolerability and hence obtain the maximum therapeutic effect without having to take into account any endangering of the motoric activity of the esophagus. Pressure monitoring allows for the optimum adjustment of the gastric band, yet also a self-control of the patient in terms of eating behavior.

The transmission device is preferably comprised of a high-frequency transmitter, and the receiving device is preferably comprised of a high-frequency receiver. The output power of the co-implanted high-frequency transmitter is relatively low to reach relatively small ranges such that the power consumption will likewise be minimal and the service life of the implant will, hence, be increased.

It is also feasible that the high-frequency transmitter is comprised of a passive transmitter and the energy required for the transmission of the detected pressure values is inductively coupled into the system from outside. Such passive systems have already been known for other implants.

In order to obtain a bidirectionality in the data transmission between the control unit and the implanted gastric band, the transmission device in the gastric band and the receiving device in the control unit may be comprised of a high-frequency transponder, which fulfils the functions of both transmitter and receiver.

According to a further characteristic feature of the invention, at least one pressure sensor is comprised of a piezoelectric sensor. The sensor can be arranged at any point in the gastric band that is suitable for measuring the pressure acting on the gastric wall, i.e., for instance, in the chamber or on the stoma-side chamber wall or the like.

If a memory is provided in the gastric band for storing the detected pressure values, the values can be temporarily stored and transmitted to a control unit for evaluation upon request. Such a memory can also serve to temporarily store the pressure values in the event of an operating failure of the control unit so as to prevent the loss of relevant data.

Likewise, a memory may be provided, on the one hand, for storing the data detected, and, on the other hand, for storing possible calculation formulas or programs in the control unit.

Furthermore, a display is preferably provided in the control unit, via which display the data, and the data derived therefrom, may be transmitted to the patient. The display may be comprised of simple light-emitting means, via which particular conditions are optically represented, or of numerical displays for the representation of the pressure values, or values derived therefrom, or of screens, via which the pressure course can be graphically represented over time.

The device for processing the pressure values received is preferably comprised of a microprocessor.

In order to obtain a temporal allocation of the data, a time module may also be provided in the control unit, as is usually the case with microprocessor applications.

To put the control unit into operation, or to switch between operating states, at least one operating element may be provided in the control unit.

In order to indicate the occurrence of particular conditions to the patient or the attending physician, a signal generator may be provided in the control unit.

Such a signal generator may, for instance, be comprised of a loudspeaker or an oscillation generator. The latter offers the advantage that, similar to the vibrations of a mobile phone, the surroundings will not notice the signal of the signal generator.

Finally, the control unit preferably comprises an interface to transmit the data, for instance, to a computer or the like. The patient will, thus, be also able to transmit the data for an evaluation to the clinic or the attending physician, for instance, via the internet or via the telephone network so as to obtain the evaluation without having to go to the clinic or the attending physician.

In an advantageous manner, the housing of the control unit is designed in the form of a watch including a suitable watch strap. In this manner, it is very convenient for the patient with the implanted gastric band to wear the control unit all the time and, hence, be constantly informed on the state of the gastric band. Likewise, data can be stored over a given period of time, say 24 hours, before being transmitted by the control unit to an evaluation device, for instance, at the attending physician, where an analysis of the data is performed.

Furthermore, a device for introducing or sucking off fluid into or from the chamber of the gastric band may be provided to optimize the pressure in the chamber of the gastric band on the basis of the detected and evaluated pressure values. In this manner, an automatic or semi-automatic system is provided, which will always optimally adjust the gastric band on the basis of the detected pressure values. The device for introducing or sucking off fluid into or from the chamber may be in the form of an implant receiving the appropriate information from the control unit in a wireless manner.

The device for introducing or sucking off fluid may also be comprised of a pump arranged in the connection between the chamber and the second chamber of the gastric band to convey fluid from the chamber into the second chamber or vice versa.

In addition, relevant information on the patient's eating behavior may be provided by the aid of a sensor for measuring the swallowing activity, which sensor is connected with a device for the wireless transmission of the detected sensor values to the control unit. Such a swallow sensor may, for instance, be comprised of a microphone or a pressure transducer glued to the patient's neck.

According to a further characteristic feature of the invention, a line for connecting the control unit with a communication device, in particular a computer or a telephone, is provided. In this manner, a data connection can be established via the interface of the control unit and said line to a communication device, and from there to further communication devices such as, for instance, the internet or a telephone network.

The second chamber of the gastric band, as a rule, is without autoregulatory function in the present gastric bands, usually formed by a port to be arranged subcutaneously and via which the fluid can be introduced into, or sucked from, the chamber of the gastric band by the aid of a subcutaneous syringe.

The two chambers of the controllable gastric band, or the chamber and port, are preferably interconnected via a duct, with at least one device for controlling the flow rate of the fluid being arrangeable in said duct. The flow-rate control device may, for instance, be comprised of a valve or pump, thus enabling the automatic control of the pressure in the chamber of the gastric band and, hence, on the gastric wall by means of the measured pressure values.

In an advantageous manner, the processing device is configured for detecting the duration and speed of an eating process. Based on the detected parameters relating to the eating process, an optimization of the band adjustment can be effected by the physician or automatically, and relevant information on the patient's eating behavior can be provided to the latter.

In this context, the processing device is preferably configured for evaluating the amplitude and duration of the detected pressure values during an eating process.

The amplitude and duration of increases in the pressure values are important indicators of excessive stress on the esophagus.

The invention is also achieved by a method for controlling an implantable gastric band, including a fluid-filled chamber, wherein the pressure on the stomach wall is measured and the amount of fluid in the chamber of the gastric band is adjusted based on the pressure detected, wherein the pressure values are continuously measured and the duration and speed of an eating process is determined based on the pressure values detected. Based on the parameters detected relating to the eating process, an optimization of the band adjustment may be effected by the physician, or automatically, or relevant information on the patient's eating behaviour may be provided to the latter.

Here, preferably, the amplitude and the duration of the increases in the pressure values during an eating process are evaluated to conclude therefrom a change of the motoric performances of the esophagus. The amplitude and the duration of the increases in the pressure values are important indicators of excessive stress on the esophagus.

Based on the determined and evaluated pressure values, the adjustment of the fluid pressure in the chamber of the gastric band can be optimized appropriately.

The invention will be explained in more detail by way of the following Figures. Therein:

Figure 3:
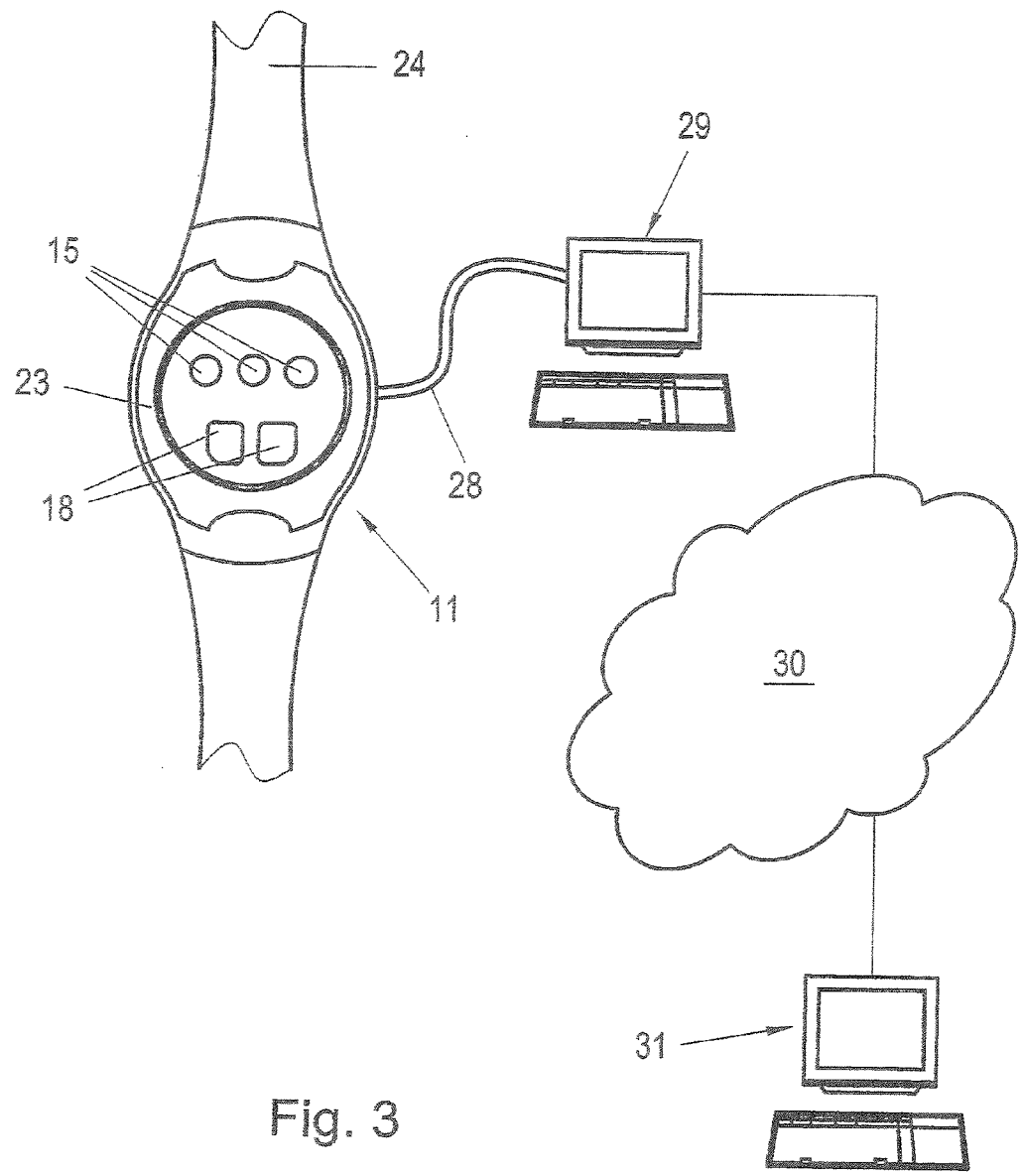
Figure 4:
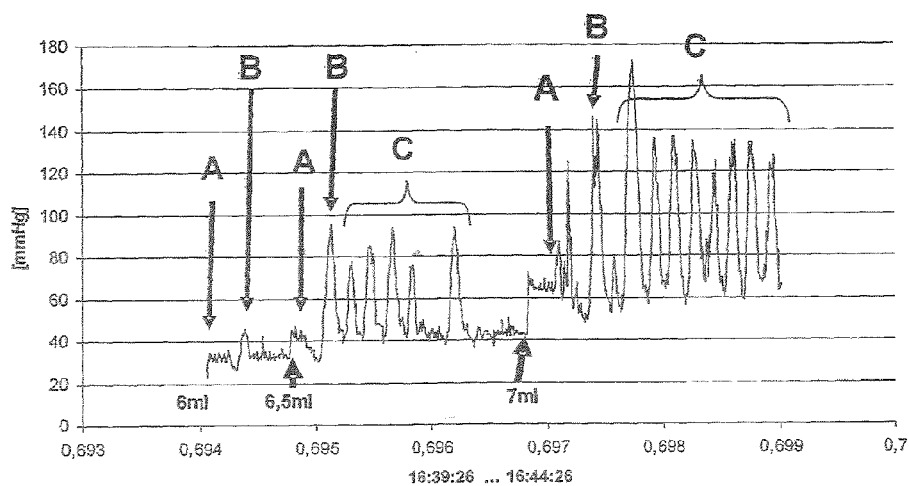
Figure 5:
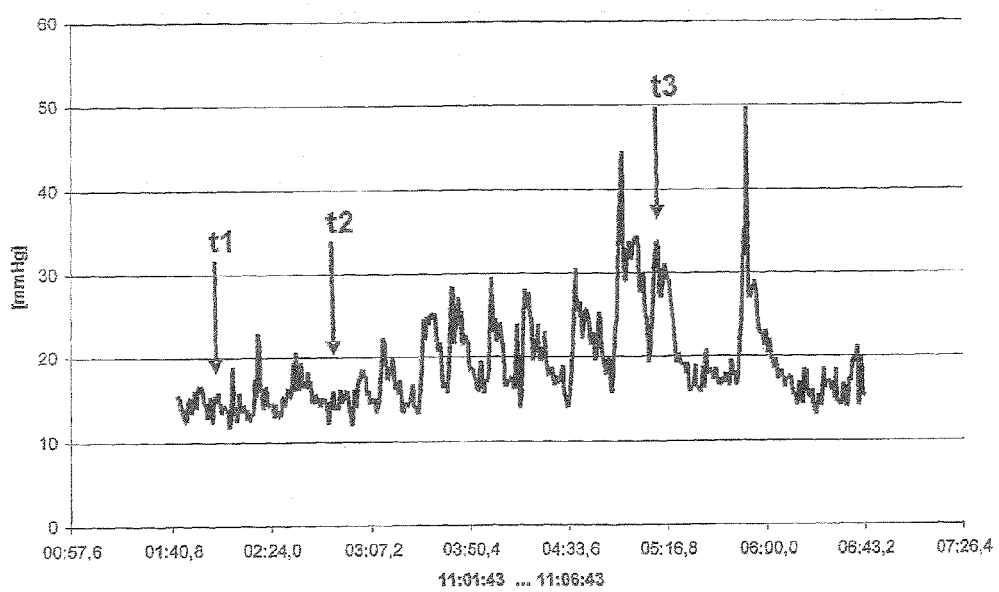

FIG. 3 schematically illustrates the data transmission from a control unit, for instance, to a computer;

FIG. 4 shows the time course of the pressure detected in the gastric band during several swallowing procedures at different fillings of the chamber of the gastric band; and FIG. 5 shows the time course of the pressure in the gastric band during an eating process.

Figure 1:
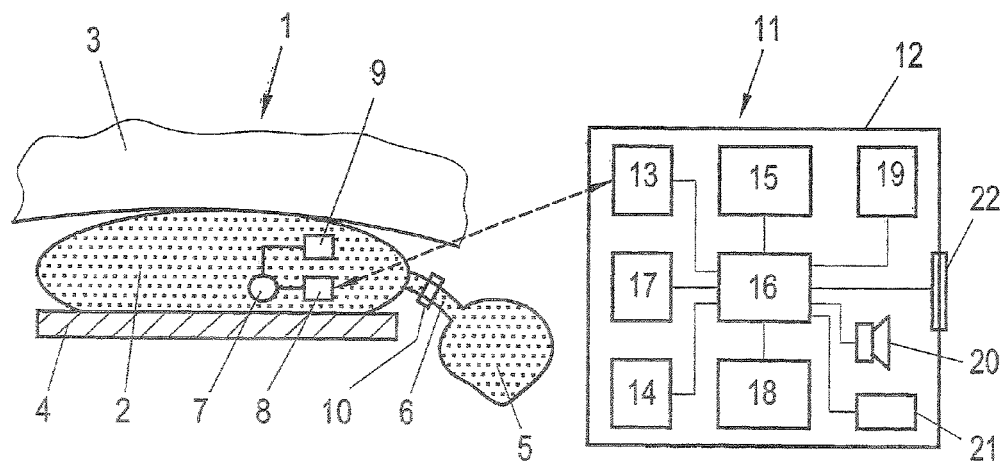
FIG. 1 is a schematic illustration of a control system comprising a gastric band including a sensor and a control unit.

FIG. 1 schematically illustrates a gastric band 1 in combination with a control unit 11, by the aid of which the pressure of the gastric band 1 can be monitored. The gastric band 1 has a nonextensible back 4. On the side of the back 4 facing the gastric wall 3 is located at least one chamber 2 which can be filled with a liquid or fluid. The chamber 2 is connected with a second chamber 5 via a duct 6. By displacing the liquid between the chambers 2 and 5, the contraction of the gastric band 1 laid around the inlet of the stomach and, hence, the pressure exerted on the stomach can be changed. The second chamber 5 can be designed as a so-called port, which is subcutaneously arranged in the lower stomach (cf. FIG. 2) to enable the supply or discharge of liquid from outside by means of a subcutaneous syringe and, hence, a variation of the amount of liquid and, as a result, the pressure in the chamber 2. To control the flow rate of the liquid or fluid from the one chamber 2 into the other chamber 5 and vice versa, a suitable device 10 for controlling the flow rate of the liquid may also be provided in the connection duct 6. This control device 10 may, for instance, be comprised of a valve or a pump (not illustrated). In the chamber 2, or at any other suitable point, such as, e.g., in the second chamber 5, at least one sensor 7 is provided to measure the pressure acting on the gastric wall 3, or a quantity proportional thereto, which sensor 7 is connected to a device 8 for the wireless transmission of the detected pressure values to a control unit 11. A memory 9 may be provided to store, or temporarily store, the pressure values detected by the pressure sensor 7. The implanted transmission device 8 may be supplied with electric power from a battery, or have a completely passive structure, with the energy required for data transmission being introduced from outside and, in particular, from the receiver of the control unit 11. In order to allow for a data transmission not only from the gastric band 1 to the control unit 11 but also the other way round, the transmission device 8 may also be comprised of a transponder.

The control unit 11 contains a device 13 for receiving the transmitted pressure data from the sensor 7 of the gastric band 1, which, too, may be designed as a transponder. In addition to a memory 14 for storing the transmitted data and also programs, a display 15 is preferably arranged in the housing 12 of the control unit 11. The received pressure values are processed via a device 16. This processing device 16 is preferably comprised of a microprocessor, microcontroller or the like. In order to be able to temporally allocate the detected and transmitted data, a time module 17 may be connected with the processing device 16. Furthermore, at least one operating element 18 may be provided to start the control unit 11 or switch between operating states.

To inform the patient, or even the physician, on the occurrence of particular conditions, a signal generator, for instance a loudspeaker 20 or an oscillation generator 21, may be provided. The components of the control unit 11 are supplied with electric power from a voltage supply 19, which is preferably comprised of a rechargeable battery.

In order to enable the transmission of data stored in the memory 14, for instance, to a computer, an interface 22 may be provided. Via such an interface 22, it is also feasible to write data into the processing device 16 or into the memory 14. The interface 22 may, for instance, be comprised of different, standardized interfaces. They may encompass both line-conducted and wireless (e.g., infrared or high-frequency) interfaces.

Figure 2:
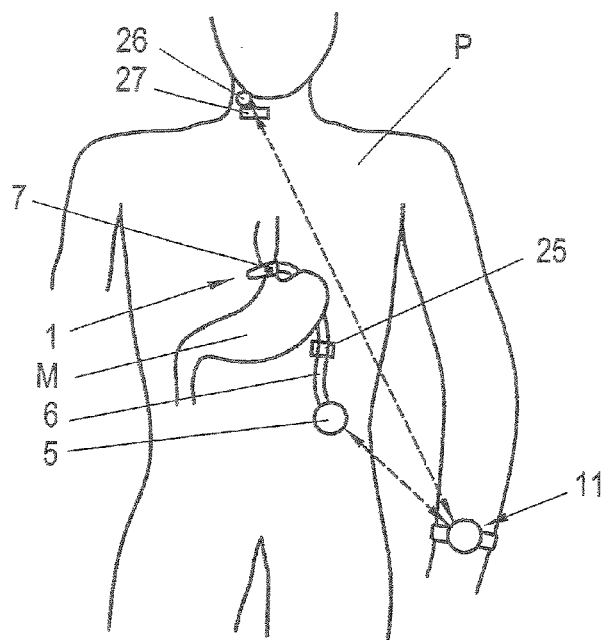
FIG. 2 is a schematic illustration of an implanted gastric band according to the invention comprising a control unit in watch form.

FIG. 2 schematically indicates an application of the gastric band 1 according to the invention comprising at least one pressure sensor 7, in which the second chamber 5 is formed by a so-called subcutaneous port, which is connected with the chamber 2 of the gastric band 1 via a duct 6 in which a pump 25 may, for instance, be arranged to control the transport of liquid from chamber 2 to chamber 5 or vice versa. The gastric band 1 encloses the entry of the stomach M of the patient P. In accordance with the invention, the data of the pressure sensor 7 are transmitted to the control unit 11, which in the illustrated example is designed in the form of a watch including a suitable watch strap (cf. FIG. 3), where they are processed and stored and displayed. In addition to the pressure sensor 7 provided in the gastric band 1, a sensor 26 for measuring the swallowing activity of the patient P may be connected with a suitable device 27 for wireless transmission, and these data, too, may be wirelessly transmitted to the control unit 11. To the patient P, the control unit 11 serves as a biofeedback instrument reflecting his/her eating behavior. Besides the duration of food intake, also other factors like the speed of food intake and the degree of chewing can be determined and indicated. A high eating speed leads to higher pressure increases in the gastric band just like poor chewing. Pressure monitoring will, thus, become an instrument of self-control in terms of eating behavior for the patient. Moreover, failures in the system caused, e.g., by a loss of liquid due to a leakage of the gastric band 1 will be immediately recognized and indicated to the patient P.

From the wearer of the gastric band 1, a change in the eating technique will be required in order to prevent unpleasant sensations or vomiting. Slow eating and good chewing while observing suitable breaks between the individual bites will be necessary. The extremely adipose patient, who would almost always suffer from a correspondingly massive eating disorder, frequently has difficulties in changing over to this correct eating technique. A continuously maintained wrong eating technique may have adverse effects on the long-term therapeutic success of the gastric band and lead to a severe motoric disorder of the esophagus peristaltic as well as a massive expansion of the esophagus. It, therefore, seems to be of great advantage for the patient to receive a permanent feedback by the control unit 11 on whether the food intake is effected properly and whether eating takes too long.

The control unit 11 processes the pressure data into a form immediately apparent to the patient and issues instant feedbacks on his eating behavior as well as warnings in the event of a malfunctioning of the gastric band 1 and signs of muscular exhaustion of the esophagus. The requirement of an immediate medical check will then be indicated. The feedbacks to the patient P can be provided via optical information means on a display 15 or by an acoustic or tactile signal generator (cf. FIG. 1).

FIG. 3 is a schematic block diagram illustrating the teletransmission of data from the control unit 11 to, for instance, a computer 31. In this case, the control unit 11 is connected by a suitable line 28, preferably via the interface 22 (cf. FIG. 1), to a communication device, for instance a computer 29. In this manner, the data contained in the control unit 11 can be transmitted to the computer 29 and, from there, to another computer 31 via a data network 30 and, in particular, the internet. The patient is, thus, able to transmit the data of his control unit 11 in a convenient and time-saving manner to a computer 31 of the clinic or the attending physician, where they will be evaluated appropriately.

The optimization of the band adjustment is an important issue to reach the maximum therapeutic effect, on the one hand, and to prevent damage to the esophagus by too long a residence time of food in the esophagus (cf. above), on the other hand. Portions of the chyme remaining in the esophagus stimulate the occurrence of secondary peristaltic waves. This secondary peristaltic tries to further convey the bolus and purge the esophagus. If this is not feasible and food particles are constantly left above the gastric band, this will over days and weeks cause mucositis involving pain, on the one hand, and lead to a motoric exhaustion and growing expansion of the esophagus, on the other hand.

To the physician, a check of the band adjustment effected by him is, therefore, of great importance. The quality of the adjustment, however, will only become apparent in daily routine during food intakes and sleeping phases. It will only then become clear whether the selected band adjustment entails too long a postprandial residence time of food particles in the esophagus, or a poor drainage of saliva during the sleep, etc. To ensure the optimum band adjustment, the recording of pressure data over a restricted period of time, say over 24 hours, is, therefore, recommended. Based on these data, which can now be very conveniently detected and transmitted, a highly precise readjustment of the band may then be effected by the physician.

FIG. 4 illustrates the time course of the pressure in the gastric band during several swallowing procedures of 15 ml of water each at three different band fillings, namely 6 ml, 6.5 ml and 7 ml. This time-pressure graph demonstrates the dependence of the secondary peristaltic on the degree of contraction of the band and, hence, impeded drainage. At each band filling, the patient must take a 15-ml sip of water (arrow A). At a band filling of 6 ml, just one single pressure increase in the gastric band occurs. This pressure increase corresponds to the primary peristaltic wave triggered by the swallowing act (arrow B). At a band adjustment of 6.5 ml, the primary peristaltic wave is followed by five secondary peristaltic waves (region C) (not triggered by a swallowing act). This hints at an already very markedly impeded drainage. At a filling volume of 7 ml, the band is no longer passable. This is reflected in the continued secondary peristaltic (region C) following upon the 15-ml water swallowing act. The optimum band filling in this case ranges between 6 and 6.5 ml.

FIG. 5 finally illustrates the time course of the detected pressure in a gastric band while eating a meal composed of a soup and dill potatoes. At time t1, the subject starts eating the soup, at time t2 the subject starts eating the potatoes. Arrow t3 marks the termination of eating. The pressure waves derived in the band interior reflect the duration of eating. Upon termination of eating, pressure waves may still be derived as a function of the extent of impeded drainage in the band interior for a different time.

Finally, it should be mentioned that heart contractions may also be detected from the timely pressure course because of the anatomic closeness of the sensor 7 to the heart, and, thus, the heart rhythm may be derived.

The invention claimed is:

1. A control system for controlling a controllable gastric band (1), comprising a control unit (11), wherein the gastric band (1) includes a non-extensible back (4) and a chamber (2) arranged on a stoma side of the back (4) and capable of being filled with a fluid, said chamber being in connection with a second chamber (5) and having at least one sensor (7) to detect pressure values on the gastric wall (3), and wherein the at least one sensor (7) is connected with a transmission device (8) for wireless transmission of the detected pressure values to the control unit (11), and wherein the control unit (11)

includes a receiving device (13) for receiving the pressure values transmitted from the at least one sensor (7) of the gastric band (1), as well as a housing (12), wherein the system comprises a memory for storing a time course of pressure values, wherein the time course comprises pressure values detected by the at least one sensor (7) over a period of time and recorded as a function of time, and a processing device (16) configured to evaluate amplitudes and durations of increases in the pressure values in the stored time course, wherein the increases correspond to primary and secondary peristaltic waves in the esophagus of a patient in whom the gastric band is implanted so as to enable automatic control of the gastric band based on the evaluated amplitudes and durations.

2. The control system according to claim 1, wherein the transmission device (8) comprises a high-frequency transmitter and the receiving device (13) comprises a high-frequency receiver.

3. The control system according to claim 2, wherein the high-frequency transmitter comprises a passive transmitter.

4. The control system according to claim 1, wherein the transmission device (8) and the receiving device (13) comprise a high-frequency transponder.

5. The control system according to claim 1, wherein the at least one sensor (7) comprises a piezoelectric sensor.

6. The control system according to claim 1, wherein the memory (9) is disposed in the gastric band (1).

7. The control system according to claim 1, comprising a display (15) in the control unit (11).

8. The control system according to claim 1, wherein the processing device comprises a microprocessor.

9. The control system according to claim 1, comprising a time module (17) in the control unit (11).

10. The control system according to claim 1, comprising at least one operating element (8) in the control unit (11).

11. The control system according to claim 1, comprising a signal generator in the control unit (11).

12. The control system according to claim 11, wherein the signal generator comprises a loudspeaker (20).

13. The control system according to claim 11, wherein the signal generator comprises an oscillation generator (21).

14. The control system according to claim 1, comprising an interface (22) in the control unit (11).

15. The control system according to claim 1, wherein the housing (12) of the control unit (11) comprises a watch (23) wherein the watch further comprises a watch strap (24).

16. The control system according to claim 1, comprising a device for introducing or sucking off fluid into or from the chamber (2) of the gastric band (1) for adjustment of the pressure in the chamber.

17. The control system according to claim 16, wherein the device for introducing or sucking off fluid comprises a pump (25) arranged in a connection (6) between the chamber (2) and the second chamber (5).

18. The control system according to claim 1, comprising a second sensor (26) for measuring swallowing activity, wherein said second sensor (26) is connected with a device (27) for the wireless transmission of detected sensor values to the control unit (11).

19. The control system according to claim 1, comprising a line (28) for connecting the control unit (11) with a communication device.

20. The control system according to claim 1, wherein the second chamber (5) of the gastric band (1) comprises a port for disposal subcutaneously.

21. The control system according to claim 1, wherein the chambers (2, 5) of the gastric band are connected with each other via a duct (6), wherein at least one device (10) for controlling the flow rate of the fluid is disposed in the duct (6).

22. The control system according to claim 1, wherein the processing device (16) is configured to evaluate the duration and speed of an eating process.

23. The control system according to claim 7, wherein the processing device (16) is configured to generate a graphical display that shows the detected pressure values as a function of time with both primary and secondary peristaltic waves on the display of the control unit.

24. The control system according to claim 1, wherein the processing device (16) is part of the control unit (11).

25. A method for controlling an amount of liquid flowing into a stomach of a patient, the method comprising the steps of:
(a) providing the system of claim 1 and positioning the gastric band of the system around the stomach of the patient so that it restricts the flow of liquid into the stomach;
(b) continuously detecting with the at least one sensor (7) pressure values on a gastric wall of the stomach over a period of time;
(c) recording and processing the time courses of the detected pressure values and evaluating amplitudes and durations of increases in pressure values in the recorded time courses, wherein the increases correspond to primary and secondary peristaltic waves in the esophagus of a patient in whom the gastric band is implanted, to determine a change of motoric performance of the esophagus; and
(d) automatically adjusting the gastric band to change an amount of restriction of flow of liquid into the stomach based on the amplitudes and durations.

26. The method according to claim 25, comprising the step of generating a display of the detected pressure values as a function of time that shows both primary and secondary peristaltic waves.

27. The method according to claim 25, wherein the restriction of flow of liquid into the stomach in step (d) comprises adjustment of fluid pressure in the chamber (2) of the gastric band.

28. A system for controlling a controllable gastric band, wherein said gastric band includes a non-extensible back, a first chamber arranged on a stoma side of the back, wherein said first chamber is capable of being filled with a fluid, and a second chamber
connected to the first chamber, the system comprising:
(a) at least one pressure sensor disposed in the first chamber of the gastric band to detect pressure values on the gastric wall;
(b) a memory for storing a time course of pressure values, wherein the time course comprises pressure values detected by the at least one pressure sensor over a period of time;
(c) a transmission device connected with the at least one pressure sensor for wireless transmission of pressure values;
(d) a control unit comprising a housing and a receiving device for receiving pressure values transmitted from the transmission device; and
(e) a processing device configured to evaluate amplitudes and durations of increases in time courses of pressure values, wherein the increases correspond to primary and secondary peristaltic waves in the esophagus of a patient in whom the gastric band is implanted.

* * * * *